United States Patent [19]

Down et al.

[11] Patent Number: 5,254,567
[45] Date of Patent: Oct. 19, 1993

[54] AMORPHOUS (QUINOLIN-2-YLMETHOXY)INDOLE COMPOUNDS WHICH HAVE USEFUL PHARMACEUTICAL UTILITY

[75] Inventors: Brian Down, Pierrefonds; John H. Hutchinson, Montreal, both of Canada

[73] Assignee: Merck Frosst Canada, Inc., Quebec, Canada

[21] Appl. No.: 973,491

[22] Filed: Nov. 9, 1992

Related U.S. Application Data

[63] Continuation-in-part of Ser. No. 793,087, Nov. 15, 1991, abandoned.

[51] Int. Cl.$^5$ ............... C07D 401/12; A61K 31/475
[52] U.S. Cl. ................................. 514/314; 546/174
[58] Field of Search ................... 546/174; 514/314

[56] References Cited

FOREIGN PATENT DOCUMENTS 0419049 3/1991 European Pat. Off. .

OTHER PUBLICATIONS

Suryanarayanan & Mitchell, Inter. J. of Pharm., 24, 1–4 (1985).
Byrn, S. R., Solid State Chem. of Drugs, pp. 10–11, Acad. Press. 1982.
List of Amorphous Pharmaceuticals, Chem. Abst., 1967–1990.

Primary Examiner—C. Warren Ivy
Assistant Examiner—Zinna N. Davis
Attorney, Agent, or Firm—Joseph F. DiPrima

[57] ABSTRACT

A form of 3-[N-(p-chlorobenzyl)-3-(t-butylthio)-5-(quinolin-2-ylmethoxy)indol-2-yl]-2,2-dimethylpropanoic acid sodium salt, obtained by freeze or spray drying, is more soluble in water than the crystalline form thereof. The compound is useful as an anti-asthmatic, anti-allergic, anti-inflammatory, or cytoprotective agent. It is also useful in treating diarrhea, hypertension, angina, platelet aggregation, cerebral spasm, premature labor, spontaneous abortion, dysmenorrhea, and migraine.

8 Claims, No Drawings

AMORPHOUS (QUINOLIN-2-YLMETHOXY)INDOLE COMPOUNDS WHICH HAVE USEFUL PHARMACEUTICAL UTILITY

CROSS-REFERENCE

This is a CIP of U.S. Ser. No. 793,087, Nov. 15, 1991, now abandoned.

BACKGROUND OF THE INVENTION

EP 419,049, Prasit et al., Mar. 27, 1991, describes a series of quinolin-2-ylmethoxy indoles useful as inhibitors of leukotriene biosynthesis. Examples 1 and 1A therein teach the synthesis of 3-[N-(p-chlorobenzyl)-3-(t-butylthio)-5-(quinolin-2-ylmethoxy)indol-2-yl]-2,2-dimethylpropanoic acid (L-686,708) as a crystalline compound. The sodium salt thereof, which is prepared by hydrolyzing the methyl ester with a base such as NaOH, can also be isolated as a crystalline solid which exhibits good solid state characteristics. such as non-hygroscopicity, physical stability, etc.; however, it exhibits very low aqueous solubility (approx. 0.005–0.03 mg/mL), which renders it non-suitable for conventional intravenous injection, and gives rise to low oral bioavailability.

SUMMARY OF THE INVENTION

An amorphous form of the sodium salt of L-686,708 has now been found which exhibits a solubility of 55 mg/mL in de-ionized water at 25° C.

DETAILED DESCRIPTION

The present invention is an amorphous compound of the formula I:

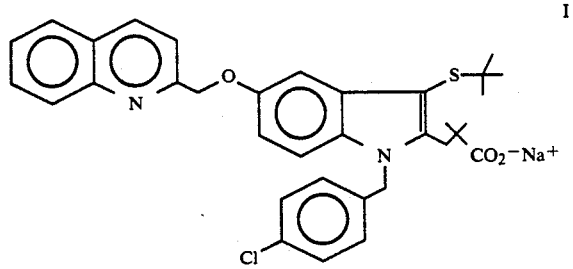

I

As used herein, "L-708 Na+ salt" will mean the crystalline form of the sodium salt of L-686,708 and "amorphous L-708" will refer to the compound of the present invention, i.e., the amorphous form of L-708 Na+ salt.

Amorphous L-708 is prepared by suspending or dissolving the free acid (L-686,708) in a mixture of water and a suitable organic co-solvent or co-solvents, such as methanol, ethanol, isopropanol, ether, acetone, 2-butanone, acetonitrile, and the like. The solution or suspension of free acid is then neutralized with one equivalent of sodium hydroxide, preferably in aqueous solution. If necessary, to obtain a homogeneous solution, the mixture may then be heated and/or additional water and organic solvent may be added as required. The bulk of the organic solvent(s) is then removed by evaporation under vacuum with moderate warming. The remaining, mostly aqueous, solvent is removed by lyophilization (freeze-drying) to leave the compound of the present invention as an amorphous powder.

If the mixture is to be lyophilized, it is preferred to continue the distillation until the mixture achieves a concentration of 77–120 mg/mL and has an oily consistency. This additional concentration both improves the efficiency of the lyophilization step and reduces the residual organic solvent concentration to <1%.

Alternatively, amorphous L-708 can be prepared from its corresponding crystalline form. L-708 Na+ salt is dissolved or suspended in a mixture of water and one or more organic co-solvents as indicated above. Once a homogeneous solution is obtained, the amorphous form is obtained by evaporation and lyophilization as described above.

The resultant amorphous material retains the biological properties of its crystalline allotrope but is highly soluble in water.

An alternative drying process is to spray dry the above homogenous solutions. Advantageously, evaporation of the organic co-solvent is not necessary prior to spray drying.

The term "amorphous" is used to describe the physical state of the sodium salt of L-686,708 obtained by drying an aqueous solution of said sodium salt as described herein. In addition to greatly increased aqueous solubility, the amorphous form is characterized by showing no X-ray powder diffraction pattern (e.g., on a Philips PW 1840 diffractometer), in contrast to the crystalline form. (A discussion of crystalline vs. amorphous states may be found in: *Solid State Chemistry of Drugs*, by S. R. Byrn, Academic Press, N.Y., 1982, pp. 10–11 and R. Suryanarayanan and A. G. Mitchell, Int. J. Pharm., Vol. 24, pp. 1–17 (1985)).

Another physical parameter useful for characterizing the present invention is differential scanning calorimetry (DSC). The amorphous material of the present invention shows a clear exotherm between 180° and 195° C., as it converts to the crystalline form. As heating is continued, there is an endotherm at 325° C. as the material melts. In contrast, the L-708 Na+ salt shows no peak in its DSC between 180° and 195° C., and shows the endothermic melting peak at 335° C.

Thermal scans were obtained on samples prepared in crimped aluminum pans under $N_2$ using a Perkin Elmer DSC-4 with a System-4 controller. The DSC was calibrated with Indium (156.6°±0.2° C.). Amorphous L-708 crystallizes at ca. 190° C. with an enthalpy of crystallization of ca. −30 kJ/mol. This is generally followed by a second smaller exotherm at ca. 259° C. ($\Delta H = -7.6$ kJ/mol).

The crystallization enthalpy at ca. 190° C. ($\Delta H$, obtained by DSC) of amorphous L-708 is related to the amount of X-ray amorphous material in the sample. In one set of experiments L-708 Na+ salt was assumed to be 100% crystalline with no enthalpy of crystallization at 190° C., while amorphous L-708 was assumed to be 100% amorphous with an enthalpy of crystallization of ca. −30 kJ/mol. 0 to 80% of ground L-708 Na+ salt was shaken with amorphous L-708. The enthalpies of crystallization of the blends were measured by DSC and plotted as a function of crystalline content. A straight line with a correlation coefficient of 0.9985 was obtained. Standard deviations varied between 0.06 and 0.7. The fact that a straight line was obtained indicates that seeding the X-ray amorphous material with ground crystalline material does not lead to nucleation and crystal growth.

Surprisingly, saturated aqueous solutions of amorphous L-708 are highly stable, i.e., they do not readily precipitate the crystalline form even when seeded with the crystalline allotrope. The solid material is also highly stable. No change in water solubility has been observed even when stored for three months at 30° C. and 60° C. at ambient humidity and at 30° C./79% relative humidity. Amorphous L-708 is also highly stable to chemical decomposition both in the solid form and in aqueous solution.

Amorphous L-708 is useful as an inhibitor of leukotriene biosynthesis in the same manner as described in EP 419,049 for L-686,708. Advantageously, it is much more bioavailable than L-708 Na+ salt. EP 419,049 is incorporated herein by reference, especially pages 5–10, 25, and 26 thereof.

Therefore, one aspect of this invention is a pharmaceutical composition comprising a therapeutically effective amount of amorphous L-708 and a pharmaceutically acceptable carrier.

Another aspect is a pharmaceutical composition as described above additionally comprising an effective amount of a second active ingredient selected from the group consisting of non-steroidal anti-inflammatory drugs; peripheral analgesic agents; cyclooxygenase inhibitors; leukotriene antagonists; leukotriene biosynthesis inhibitors; $H_1$- or $H_2$-receptor antagonists; antihistaminic agents; prostaglandin antagonists; and ACE antagonists. Especially preferred is such a pharmaceutical composition wherein the second active ingredient is a non-steroidal anti-inflammatory drug. Also especially preferred is such a pharmaceutical composition wherein the weight ratio of amorphous L-708 to said second active ingredient ranges from about 1000:1 to 1:1000.

Another aspect of this invention is a method of preventing the synthesis, the action, or the release of SRS-A or leukotrienes in a mammal which comprises administering to said mammal an effective amount of amorphous L-708, especially wherein the mammal is man.

Another aspect is a method of treating asthma in a mammal comprising administering to a mammal in need of such treatment a therapeutically effective amount of amorphous L-708, especially wherein the mammal is man.

Another aspect of this invention is a method of treating inflammatory diseases of the eye in a mammal which comprises administering to a mammal in need of such treatment a therapeutically effective amount of amorphous L-708, especially wherein the mammal is man.

The invention is further defined by reference to the examples, which are intended to be illustrative and not limiting. Temperatures are in degrees Celsius.

Preparations 1 and 2 appear in EP 419,049 as Examples 1 and 1A and are copied here for convenience. Starting materials also appear in EP 419,049.

PREPARATION 1

3-[N-(p-Chlorobenzyl)-3-(t-butylthio)-5-(quinolin-2-ylmethoxy)indol-2-yl]-2.2-dimethylpropanoic acid Step A:
3-[N-p-Chlorobenzyl-3-(t-butylthio)-5-methoxyindol-2-yl]-2,2-dimethylpropanoic acid methyl ester To a solution of 39 g of methyl 5-(t-butylthio)-2,2-dimethyl-4-oxopentanoate in a mixture of 300 mL of toluene and 150 mL of glacial acetic acid was added 15 g of NaOAc and 50 g of 1-(4-methoxyphenyl)-1-(p-chlorobenzyl)hydrazine hydrochloride. The reaction was maintained with stirring at room temperature for 3 days under argon in the dark. The mixture was poured into 3 L of $H_2O$ and extracted with $3\times500$ mL of EtOAc. The ethyl acetate was washed with $3\times500$ mL of water then solid $NaHCO_3$ was added. The mixture was filtered and the filtrate washed twice with water. The organic phase was dried over $MgSO_4$ and evaporated to dryness to provide the title compound. m.p. 102°–103° C.

Step B:
3-[N-(p-Chlorobenzyl)-3-(t-butylthio)-5-methoxyindol-2-yl]-2,2-dimethylpropanoic acid The compound from Step A was hydrolysed using 325 mL of THF, 600 mL of MeOH and 325 mL of 1.0M LiOH. The solution was heated to 80° C. for 3 h. The solution was acidified with 1N HCl and extracted with $3\times200$ mL of EtOAc. The organic phase was washed with water ($2\times150$ mL) and dried over $MgSO_4$. The solution was evaporated to dryness to provide the title compound. m.p. 190°–191° C.

Anal C, H, N: Calc. C 65.27; H 6.57; N 3.04. Found C 65.28; H 6.58; N 3.04.

Step C: Methyl 3-[N-(p-chlorobenzyl)-5-hydroxy-3-(t-butylthio)indol-2-yl]-2,2-dimethylpropanoate A solution of 61 mL of t-butylthiol in 650 mL of dry HMPA at 0° C. was treated portionwise with 26 g of 50% NaH in mineral oil after removal of oil with hexane. The reaction was stirred at RT for 30 mins and 46 g of the compound from Step B was added.

The reaction was then heated under $N_2$ at 175° C. for 5 hours. The solution was cooled, and poured onto crushed ice, after which it was treated with 2 N HCl to pH 5 and extracted with EtOAc ($3\times500$ mi). The organic phase was washed with $H_2O$ ($3\times200$ mi) dried ($MgSO_4$) and evaporated. The residue was dissolved in 300 mL of ether and ethereal diazomethane was added until all acid was consumed. The excess solvent was removed and the oily residue triturated with hexane to leave a crystalline mass which was recrystallized from EtOAc/hexane to provide the title compound as a white crystalline solid, m.p. 170°–171° C.

Step D: Methyl 3-[N-(p-chlorobenzyl)-3-(t-butylthio)-5-(quinolin-2-ylmethoxy)indol-2-yl]-2,2-dimethylpropanoate Methyl 3-[N-(p-chlorobenzyl)-5-hydroxy-3-(t-butylthio)indol-2-yl]-2,2-dimethylpropanoate (33.6 g) from Step C was dissolved in 500 mL of dry DMF and the solution was charged with 2.4 g of KI, 30.3 g of $K_2CO_3$, 4.77 g of $Cs_2CO_3$ and 23.5 g of 2-(chloromethyl)quinoline hydrochloride. The reaction was stirred at RT, under $N_2$, for 72 hours then it was poured into water (1.5 L), acidified with 1N HCl and extracted ($3\times200$ mL) with $CH_2Cl_2$. The organic phase was washed with $H_2O$ ($3\times150$ mi), dried and evaporated. The residue was dissolved in hot EtOAc and upon cooling crystallized to deposit 22.0 g of the title compound, m.p. 166°–167°C.

Step E:
3-[N-(p-Chlorobenzyl)-3-(t-butylthio)-5-(quinolin-2-ylmethoxy)indol-2-yl]-2,2-dimethylpropanoic acid Using the hydrolytic procedure of Step B but substituting the ester of Step D for the ester of Step A provided the title compound, which was recrystallized from 1:1 EtOAc/hexane. m.p. 208° C.

Anal C, H, N: Calc. C 69.55; H 6.01; N 4.77. Found C 69.77; H 6.05; N 4.70.

PREPARATION 2

3-[N-(p-Chlorobenzyl)-3-(t-butylthio)-5-(quinolin-2-ylmethoxy)indol-2-yl]-2,2-dimethylpropanoic acid Step A: N-Acetyl-4-(quinolin-2-ylmethoxy)aniline A mixture containing 2-(chloromethyl)quinoline hydrochloride (100.0 g), 4-acetamidophenol (70.69 g) and milled anhydrous potassium carbonate (194 g) was stirred in DMF (1.2 L) using a mechanical stirrer for 48 hours. The mixture was carefully poured onto ice/water (3 L) with vigourous stirring. After the ice had melted, the solid was filtered and rinsed thoroughly with water. It was recrystallized from 95% ethanol and filtered to give the title compound in three crops.

Step B: 4-(Quinolin-2-ylmethoxy)aniline

A suspension of N-acetyl-4-(quinolin-2-yl-methoxy)aniline (Step A, 108.9 g) in 1 L of 95% ethanol containing 10 M KOH (120 ml) was heated at reflux under nitrogen in a heating mantle. When the hydrolysis was complete (approx. 36 h), the reaction mixture was cooled and ethanol was partially removed under vacuum. The mixture was then diluted with water (200 mL) and the fine off-white crystals were collected and thoroughly rinsed with water. The material, after air-drying, yielded the title compound which was used as such in the next step.

Step C: 4-(Quinolin-2-ylmethoxy)phenylhydrazine

A quantitiy of 84 g of 4-(quinolin-2-yl-methoxy)aniline from Step B was suspended in 300 mL of deionized $H_2O$ and 84 mL of 12 M HCl. The suspension was stirred vigourously to obtain a fine particle suspension. Then a precooled solution (5° C.) of 23.88 g of sodium nitrite dissolved in 75 mL of deionized $H_2O$ was added dropwise to the suspension at 5° C. over 25 minutes. The solution was stirred at 5° C. for 60 min to obtain the diazonium salt as a clear brown solution. The presence of excess $HNO_2$ was confirmed by KI-starch paper, and the pH of the solution was about 3.0. If a white suspension persisted after 1 h, the mixture was filtered through a glass wool plug, to give the diazonium salt in the filtrate.

In the meantime a sodium hydrosulfite solution was-prepared by dissolving 321 g of sodium hydrosulfite (approx. 85% purity) in 2 L of deionized water, and cooled at 0° to 5° C. To this solution were added 15 mL of 2N NaOH and 2 L of ether. The biphasic solution was kept near 0° C. by additon of crushed ice and was stirred vigourously. To this solution was added dropwise the diazonium salt solution with stirring maintained throughout. At the end of the addition an orange solid was formed and 600 mL of NaOH (2N) was added over 30 minutes. The reaction was finally stirred for 60 minutes at 25° C. The solid was collected, suspended in ether (1 L) and filtered. The process was repeated with 2 L of water to yield the title compound as a pale yellow solid after freeze-drying overnight. m.p. 73°-85° C. (dec).

Step D:
1-(p-Chlorobenzyl)-1-[4-(quinolin-2-yl-methoxy)-phenyl]hydrazine

A quantity of 10 g of 4-(quinolin-2-yl-methoxy)-phenylhydrazine from Step C was added to a solution of 10.5 mL of diisopropylethylamine and 150 mL of $CH_2Cl_2$. To the yellow suspension was added 9.11 g of p-chlorobenzyl chloride followed by 3.64 g of $Bu_4NBr$ and 50 mL of $CH_2Cl_2$. The reaction was stirred for approximately 24 hours. When no starting material remained, the reaction was diluted with $H_2O$ and extracted 3 times with $CH_2Cl_2$. The combined organic phase was washed once with water and dried ($MgSO_4$), filtered and evaporated to dryness. The solid residue was dried under vacuum overnight prior to being swished in ether/methanol 90/10 to give the title compound as a pale yellow solid. m.p. 130° C.

Step E:
3-[N-(p-Chlorobenzyl)-3-(t-butylthio)-5-(quinolin-2-ylmethoxy)indol-2-yl]-2,2-dimethylpropanoic acid The methyl ester of the title compound was prepared according to the method described in Step A of Example 1 but using the phenylhydrazine from Step D of Example 1A as starting material.

The title compound was prepared under the conditions described in Step B of Example 1.

PREPARATION 3

Crystalline
3-[N-(p-chlorobenzyl)-3-(t-butylthio)-5-(quinolin-2-ylmethoxy)indol-2-yl]-2.2-dimethylpropanoic acid, sodium salt (L-708 Na+ Salt by Hydrolysis of Ester)

A mixture of the methyl ester of the title acid (Preparation 1, Step D) (6.25 kg, 10.4 moles) and EtOH (absolute, 45 L) was warmed to 50° C. and a solution of NaOH (2.29 L of a 5N solution, 11.4 moles) in $H_2O$ (5 L) was added. The reaction was heated to reflux and held at this temperature for 41 hours. The progress of the reaction was monitored by HPLC using a Zorbax RX column, a mobile phase consisting of 0.1% phosphoric acid:acetonitrile (20:80) at 1.15.mL/min, with UV detection at 220 nm. Additional NaOH (103.8 mL of a 5N solution, 0.52 moles) was added and the reaction was held at reflux for 24 hours, then cooled to 60° C. EtOH:H2O (25 L of a 90:10 mixture) was added and the reaction was filtered. The filtrate was azeotropically distilled to remove the water. Ethanol was added, as needed, during the distillation to maintain the volume above 62.5 L. The distillation was monitored for water content by Karl Fischer titration. The reaction was concentration to 37.5 L, cooled to room temperature, then filtered. The filter cake was washed with cold (5° C.) EtOH (5×3.75 L) and dried under vacuum at 50° C. for 72 hours, providing 5.58 kg of the title compound (88% yield).

EXAMPLE 1

Amorphous
3-[N-(p-chlorobenzyl)-3-(t-butylthio)-5-(quinolin-2-ylmethoxy)indol-2-yl]-2,2-dimethylpropanoic acid, sodium salt (Amorphous L-708 from the Free Acid)

To a two liter Erlenmeyer flask was added 12.25 gm (20.86 mmol) of the title acid (Preparation 1) followed by 100 mL of EtOH and 100 mL of $H_2O$. The resulting suspension was stirred and 20.86 mL of 1N aqueous NaOH (20.86 mmol) was added. The pH was approximately 8. To dissolve the bulk of the suspended material, an additional 100 mL of EtOH and 300 mL of $H_2O$ were added with stirring. The resulting mixture was filtered to remove a small amount of insoluble material, and the bulk of the EtOH removed from the filtrate on a rotary evaporator at between 30° C. and 50° C. The resulting solution was lyophilized at −78° C. to yield the title compound.

Purity by HPLC analysis: 98.9-99.2% Solubility in water: at least 3 mg/mL (at least 5 mM) (not tested higher).

EXAMPLE 2

Amorphous
3-[N-(p-chlorobenzyl)-3-(t-butylthio)-5-(quinolin-2-ylmethoxy)indol-2-yl]-2,2-dimethylpropanoic acid, sodium salt (Amorphous L-708 from L-708 Na+ Salt)

Crystalline 3-[N-(p-chlorobenzyl)-3-(t-butylthio)-5-(quinolin-2-ylmethoxy)indol-2-yl]-2,2-dimethylpropanoic acid, sodium salt, (25 g) was dissolved in EtOH (2.75 L) at 20° C. Water (1 L) was added thereto and then the volume was reduced to 0.5 L in a rotary evaporator. The remaining solution was lyophilized in a Virtis 10 SRC lyophilization chamber at −42° C. to yield the title compound.

Purity by HPLC analysis: 99.4%.
Amorphous by X-ray diffraction.

EXAMPLE 3

Amorphous
3-[N-(p-chlorobenzyl)-3-(t-butylthio)-5-(quinolin-2-ylmethoxy)indol-2-yl]-2,2-dimethylpropanoic acid, sodium salt (Amorphous L-708 from L-708 Na+ Salt)

Crystalline 3-[N-(p-chlorobenzyl)-3-(t-butylthio)-5-(quinolin-2-ylmethoxy)indol-2-yl]-2,2-dimethylpropanoic acid, sodium salt, (6 g) was dissolved in EtOH (240 ml) and H$_2$O (1 L) preheated to about 90° C., and then the volume was reduced to 0.9 L in a rotary evaporator. The remaining solution was lyophilized in a Virtis 10 SRC lyophilization chamber at -42° C. to yield the title compound.

Purity by HPLC analysis: 99.4%.
Amorphous by X-ray diffraction.

EXAMPLE 4

Amorphous
3-[N-(p-chlorobenzyl)-3-(t-butylthio)-5-(quinolin-2-ylmethoxy)indol-2-yl]-2,2-dimethylpropanoic acid, sodium salt (Amorphous L-708 from L-708 Na+ Salt)

A 50 L 3-necked flask carrying a thermometer probe was fitted with a mechanical stirrer, a nitrogen inlet through the top of a reflux condenser, and a downward condensor with a receiving flask and placed in a steam mantle. The flask was charged with 22 L of H$_2$O, 2 L of absolute EtOH, and 1099 g of the crystalline form of the title compound. After addition of a further 3 L of absolute EtOH, the mixture was stirred at 81°-82° C. until a clear solution was obtained. (about 20 min.). The-receiving flask was cooled in dry ice and a vacuum of −100 KPa was applied to the stirred solution through the receiving flask. Steam heating was continued in order to maintain the temperature at 17° C. Evaporation was continued until the solution started to become cloudy (about 2 hr.). The mixture was vacuum filtered through a sintered glass funnel, and the filtrate (17.5 L) was divided among 6 lyophilization trays (18.25×23.75 in.). The trays were placed in the cold lyophilization chamber (Virtis) and 2.5 hr. later, with the shelf temperature at −55° C., the vacuum was turned on.

| Lapsed time (hr.) | Shelf Temp. (°C.) |
| --- | --- |
| 0 | −55° |
| 4 | −25° |
| 17.5 | −15° |
| 66.5 | 0° |
| 98.5 | 25° |
| 114.5 | 30° |
| 140.5 | 30° |

The freeze-dried title product weighed 1084 g.

EXAMPLE 5

Amorphous
3-[N-(p-chlorobenzyl)-3-(t-butylthio)-5-(quinolin-2-ylmethoxy)indol-2-yl]-2,2-dimethylpropanoic acid, sodium salt (Spray Drying)

Crystalline 3-[N-(p-chlorobenzyl)-3-(t-butylthio)-5-(quinolin-2-ylmethoxy)indol-2-yl]-2,2-dimethylpropanoic acid, sodium salt (15 g) was dissolved in 360 mL of 20% ethanol/water by heating at reflux for 30 mins. The solution was cooled to 40°-50° C. and fed uniformly over 30 minutes to a BUCHI Model 190 Mini Spray Drier to yield 8 g of product. Drying was at inlet and outlet air temepratures of 150° C. and 104° C., respectively. The dried product was amorphous by X-ray diffraction and contained 1.4% water by Karl Fischer and 0.01% ethanol by gas chromatography analyses.

EXAMPLE 6

Solubility of Amorphous L-708

Solubility was measured by stirring 100 mg/mL in water (10 ml) of amorphous L-708 at room temperature. At 48 hrs. 1 mL of the suspension was drawn and centrifuged. The supernatant was diluted and content of amorphous L-708 was measured by both U.V. spectrophotometry and by HPLC. This gave a concentration of 55 mg/mL.

EXAMPLE 7

Amorphous
3-[N-(p-chlorobenzyl)-3-(t-butylthio)-5-(quinolin-2-ylmethoxy)indol-2-yl]-2,2-dimethylpropanoic acid, sodium salt (Amorphous L-708 from L-708 Na+ Salt)

58 L H$_2$O was heated to 81° C., then 15 L EtOH and 3249 g of the crystalline form of the title compound were added. When the solution became clear (75° C.), it was cooled to ambient and the EtOH was distilled under approximately 25 mm vacuum. The temperature ranged from 18°-21° C. Distillation was continued until a 32 L slurry remained (approximately 100 mg/mL). The slurry was divided among 6 trays of a Virtis freeze dryer and frozen overnight at 70° C. Then the vacuum was turned on to 30 μm, following which the shelf was warmed to 15° C. and held at that temperature for 46 hours. The shelf was warmed to 30° C. over 2 hours and held there for 18.5 hours. The residual ethanol by $^1$H NMR was 0.9%. The trays were then heated to 65° C. for 19 hours in a Hull vacuum dryer and yielded the freeze-dried title product; 3161 g. Residual ethanol by $^1$H NMR was 0.6%.

What is claimed is:

1. Amorphous 3[N-(p-chlorobenzyl)-3-(t-butylthio)-5-(quinolin-2-ylmethoxy)indol-2-yl]-2,2-dimethylpropanoic acid, sodium salt.

2. A compound of claim 1 having a solubility in deionized water at 25° C. of 55 mg/mL.

3. A pharmaceutical composition comprising a therapeutically effective amount of a compound of claim 1 and a pharmaceutically acceptable carrier.

4. The pharmaceutical composition of claim 3 additionally comprising an effective amount of a second active ingredient selected from the group consisting of non-steroidal anti-inflammatory drugs; peripheral analgesic agents; cyclooxygenase inhibitors; leukotriene antagonists; leukotriene biosynthesis inhibitors; $H_1$- or $H_2$-receptor antagonists; antihistaminic agents; prostaglandin antagonists; and ACE antagonists.

5. A pharmaceutical composition according to claim 4 wherein the second active ingredient is a non-steroidal anti-inflammatory drug.

6. A pharmaceutical composition of claim 5, wherein the weight ratio of said compound of claim 1 to said second active ingredient ranges from about 1000:1 to 1:1000.

7. A method of preventing the synthesis, the action, or the release of SRS-A or leukotrienes in a mammal which comprises administering to said mammal an effective amount of a compound of claim 1.

8. The method of claim 7 wherein the mammal is man.

* * * * *